(12) United States Patent
Sun et al.

(10) Patent No.: US 11,390,895 B2
(45) Date of Patent: Jul. 19, 2022

(54) METHOD FOR PREPARING PHOSPHATIDYLSERINE BY ULTRASONIC-ASSISTED ENZYMATIC HYDROLYSIS

(71) Applicant: NANTONG LICHENG BIOLOGICAL ENGINEERING CO. LTD, Nantong (CN)

(72) Inventors: Yi Sun, Nantong (CN); Hongzhi Xia, Nantong (CN); Jiangbo Li, Nantong (CN); Bo Tang, Nantong (CN); Feng Jin, Nantong (CN); Yulei Zhu, Nantong (CN)

(73) Assignee: NANTONG LICHENG BIOLOGICAL ENGINEERING CO. LTD, Nantong (CN)

( * ) Notice: Subject to any disclaimer, the term of this patent is extended or adjusted under 35 U.S.C. 154(b) by 810 days.

(21) Appl. No.: 16/320,947

(22) PCT Filed: Dec. 28, 2018

(86) PCT No.: PCT/CN2018/124581
§ 371 (c)(1),
(2) Date: Jan. 25, 2019

(87) PCT Pub. No.: WO2020/133126
PCT Pub. Date: Jul. 2, 2020

(65) Prior Publication Data
US 2021/0355513 A1 Nov. 18, 2021

(30) Foreign Application Priority Data
Dec. 27, 2018 (CN) .......................... 201811607741.0

(51) Int. Cl.
C12P 13/06 (2006.01)

(52) U.S. Cl.
CPC ....... *C12P 13/06* (2013.01); *C12Y 301/04004* (2013.01)

(58) Field of Classification Search
CPC .................... C12P 13/06; C12Y 301/04004
See application file for complete search history.

(56) References Cited

FOREIGN PATENT DOCUMENTS

| CN | 103555783 | * | 2/2014 |
| CN | 107142289 | * | 9/2017 |

OTHER PUBLICATIONS

Alain-Yvan Bélanger, Therapeutic Electrophysical Agents: Evidence Behind Practice, Third Edition, Chapter 20, pp. 379-410, 2014.*

* cited by examiner

*Primary Examiner* — Delia M Ramirez
(74) *Attorney, Agent, or Firm* — CBM Patent Consulting, LLC

(57) ABSTRACT

An ultrasonic-assisted method for preparing phosphatidylserine, comprising the following steps: adding 100-130 parts of phospholipid into a mixture of 150-200 parts of L-serine, 10-20 parts of anhydrous calcium chloride and 400-500 parts of pure water, adding 20-25 parts of phospholipase D for enzymatic hydrolysis reaction, and applying ultrasound in the enzymatic hydrolysis reaction for treatment. The present invention uses an ultrasonic treatment technology to assist phospholipase D to act on phosphatidylcholine and serine to undergo an enzymatic hydrolysis reaction to prepare phosphatidylserine, and at the same time, the ultrasonic frequency, ultrasonic intensity, ultrasonic power, ultrasonic time, ultrasonic temperature, enzyme activity and other parameters are controlled synergistically, so that the enzymatic hydrolysis conversion rate is 98% or higher.

7 Claims, 3 Drawing Sheets

METHOD FOR PREPARING PHOSPHATIDYLSERINE BY ULTRASONIC-ASSISTED ENZYMATIC HYDROLYSIS

This application is the U.S. national phase of International Application No. PCT/CN2018/124581 filed on 28 Dec. 2018 which designated the U.S. and claims priority to Chinese Application No. CN201811607741.0 filed on 27 Dec. 2018, the entire contents of each of which are hereby incorporated by reference.

TECHNICAL FIELD

The present invention relates to a method for preparing phosphatidylserine, and especially relates to an ultrasonic-assisted method for preparing phosphatidylserine.

BACKGROUND ART

Phosphatidylserine (PS), also known as complex nervonic acid, referred to as PS, was first extracted and determined in nature by Jordi Folch in 1942. Phosphatidylserine is a kind of ubiquitous phospholipid, usually located in the inner layer of a cell membrane, especially in the nervous system of a human body. It is one of the important components of the cell membrane in the brain and plays an important role in regulating various physiological functions of the brain.

Phosphatidylserine is known as another emerging "smart nutrient" after choline and DHA. In 2010, it was approved by the Ministry of Health of the People's Republic of China as a new resource food. Phosphatidylserine regulates nerve impulse transmission, enhances the efficiency of neurotransmitters that transmit brain signals, and stimulates the activation of the brain. Specifically, the main functions of phosphatidylserine are to improve brain vitality, prevent senile dementia, improve brain function, concentrate attention, improve academic performance, reduce stress hormone secretion, relieve stress; repair brain damage, promote recovery from brain fatigue, and balance emotions.

At present, a preparation method of preparing phosphatidylserine is mainly a bio-enzymatic conversion method, in which the matrix phosphatidylcholine undergoes a transphosphatidyl reaction with L-serine under the action of phospholipase D to form the phosphatidylserine. During the reaction, the level of phospholipase D activity and the degree of emulsification mixing of the reaction matrix directly affect the reaction effect, and if the emulsification is insufficient, the conversion rate will decrease.

Ultrasonic wave is a kind of longitudinal wave, which has the dual properties of wave and energy. When the ultrasonic wave acts inside liquid, it will produce a cavitation effect, generate strong shock wave and micro jet, and cause violent impact between liquid particles. Such intense interaction between particles can accelerate mass transfer and heat transfer of a system, and plays a good stirring role, so that two immiscible liquids are fully emulsified to accelerate dissolution of solutes. Different enzyme molecules have different stereoscopic conformations, and the same enzyme molecules have different conformations in different environments. Since phospholipids are difficult to emulsify in a low temperature solution, they cannot be sufficiently contacted with an enzyme solution, thereby affecting the enzymatic conversion rate. However, when the temperature is raised, the enzyme activity is greatly reduced. Therefore, when an ultrasonic assisting technique is used to promote the enzymatic efficiency, the ultrasonic assisting technique under the conventional experimental conditions does not have the effect of improving the enzymatic efficiency of phospholipase D.

SUMMARY OF THE INVENTION

Object of the invention: An object of the present invention is to provide an ultrasonic-assisted method for preparing phosphatidylserine by changing the structure of a substance by ultrasonic vibration and expanding the contact area of a matrix with an enzyme.

Technical scheme: The ultrasonic-assisted method for preparing phosphatidylserine provided by the present invention comprises the following steps: adding 100-130 parts of phospholipid into a mixture of 150-200 parts of L-serine, 10-20 parts of anhydrous calcium chloride and 400-500 parts of pure water, adding 20-25 parts of phospholipase D for an enzymatic hydrolysis reaction, and applying ultrasound in the enzymatic hydrolysis reaction for treatment.

Ultrasonic frequency is 20-40 kHz; ultrasonic intensity is 40-60 W/m$^2$; ultrasonic power is 400-600 W; ultrasonic time is 10-20 min; ultrasonic temperature is 35-55° C.; and enzyme activity is 30-60 U/ml.

Preferably, the ultrasonic frequency is 20-30 kHz; the ultrasonic intensity is 40-50 W/m$^2$; the ultrasonic power is 400-500 W; the ultrasonic time is 15-20 min; the ultrasonic temperature is 35-45° C.; and the enzyme activity is 30-50 U/ml.

When the ultrasonic power is too low, the effect of mixing phospholipid with enzyme solution is poor, which affects the conversion rate of a matrix; when the ultrasonic frequency is too high, the activity of phospholipase D is damaged, which results in great decrease in the conversion rate; when the intensity of ultrasonic treatment is too high, water molecules can be ionized to generate free radicals, and these free radicals enter the active center of the enzyme, destroy the conformation of the enzyme, and damage the activity of phospholipase D, resulting in great decrease in the conversion rate. Therefore, with appropriate power and intensity, the addition of ultrasound intervention can optimize the mixing effect and reduce the phospholipid viscosity. However, orthogonal experiments show that even under strict control of power, intensity and reaction temperature, if the enzyme activity, ultrasonic frequency and time are not up to standard, the conversion rate is still low, and the advantages of ultrasonic treatment in preparation of phosphatidylserine by enzymatic hydrolysis cannot be exploited. Therefore, the above conditions must be met at the same time.

Further, the time of the enzymatic hydrolysis reaction is 2-4 hours. Preferably, the time of the enzymatic hydrolysis reaction is 2-3 hours.

Preferably, the temperature at the start of the enzymatic hydrolysis is 35-45° C. At the beginning of the enzymatic hydrolysis reaction, when the temperature is lower than 35° C., although the enzyme activity is higher, the phospholipid is very viscous and the mixing effect is poor, resulting in a low conversion rate; when the temperature is 35-45° C., the enzyme activity is higher, and the mixing effect of feed liquid is better, resulting in a conversion rate of 93%; and especially, when the temperature is 45° C., the conversion rate reaches 98%.

Further, the phospholipid is soybean phospholipid in which the phosphatidylcholine content is 54-55%.

Preferably, the intervention time for applying ultrasound is 0-0.5 hour at the start of the enzymatic reaction.

Advantageous Effects: Compared with the prior art, the present invention has the following advantages: an ultrasonic treatment technology is used to assist phospholipase D to act on phosphatidylcholine and serine to undergo the enzymatic hydrolysis reaction to prepare phosphatidylserine, and at the same time, the ultrasonic intensity, ultrasonic frequency, temperature and time of treatment, enzyme activity and other parameters in the ultrasonic treatment process are controlled synergistically, so that enzymatic hydrolysis conversion rate is 98% or higher.

DETAILED DESCRIPTION OF THE INVENTION

The specific examples of the present invention will be described in detail below with reference to the accompanying drawings.

Example 1

Figure 1:
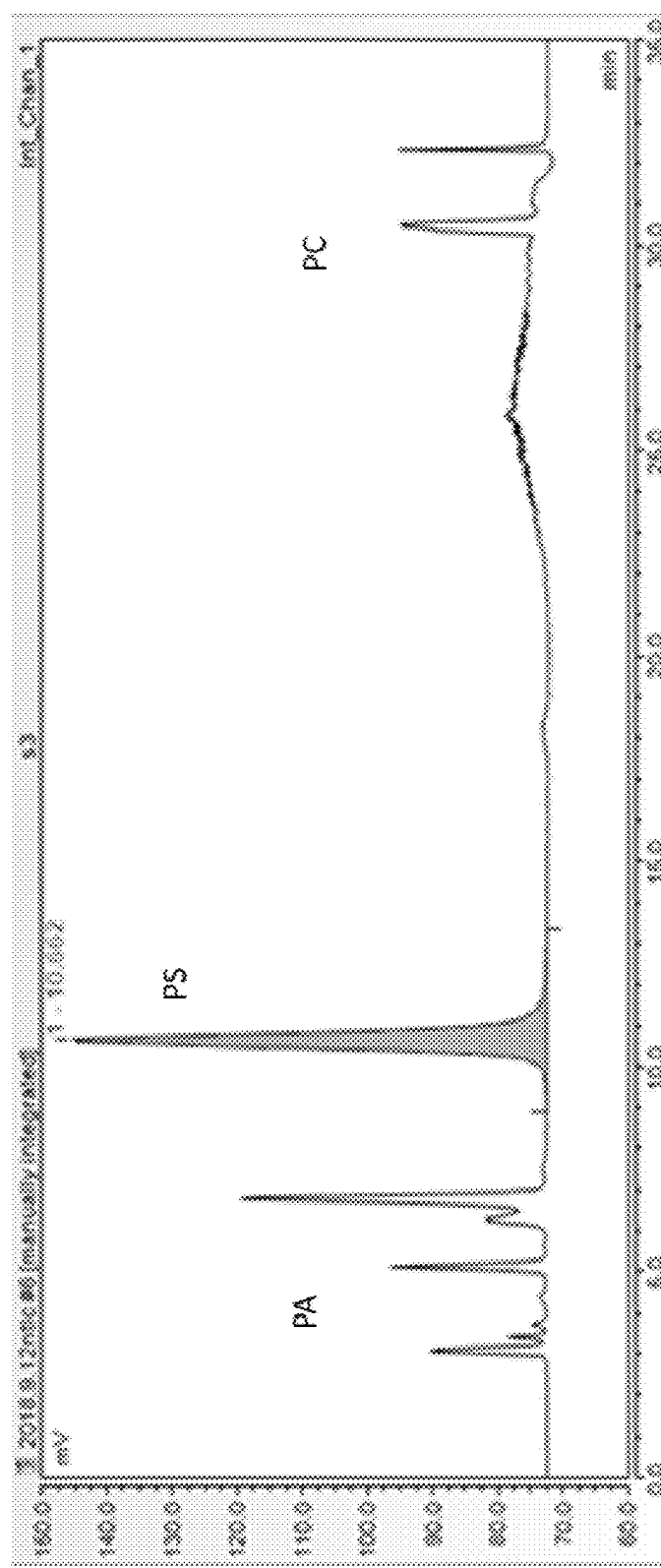
FIG. 1 is a graph showing the results of the reaction of example 1.

Adding the following substances by weight to a container: 150 g of L-serine, 10 g of anhydrous calcium chloride and 450 ml of pure water at a temperature 35° C.; adding 100 g of phospholipid which is soybean phospholipid in which the phosphatidylcholine content is 55%; performing stirring for 10 minutes; adding 20 ml of phospholipase D with the activity of 20 U/ml; applying ultrasound in an enzymatic hydrolysis process, wherein ultrasonic power is 400 W, ultrasonic intensity is 40 W/cm$^2$, ultrasonic frequency is 40 kHz, ultrasonic treatment time is 5 minutes, and enzymatic hydrolysis time is 2 hours. When enzymatic hydrolysis ends, the conversion rate of phosphatidylcholine is 90%, and reaction results are shown in FIG. 1.

Example 2

Figure 2:
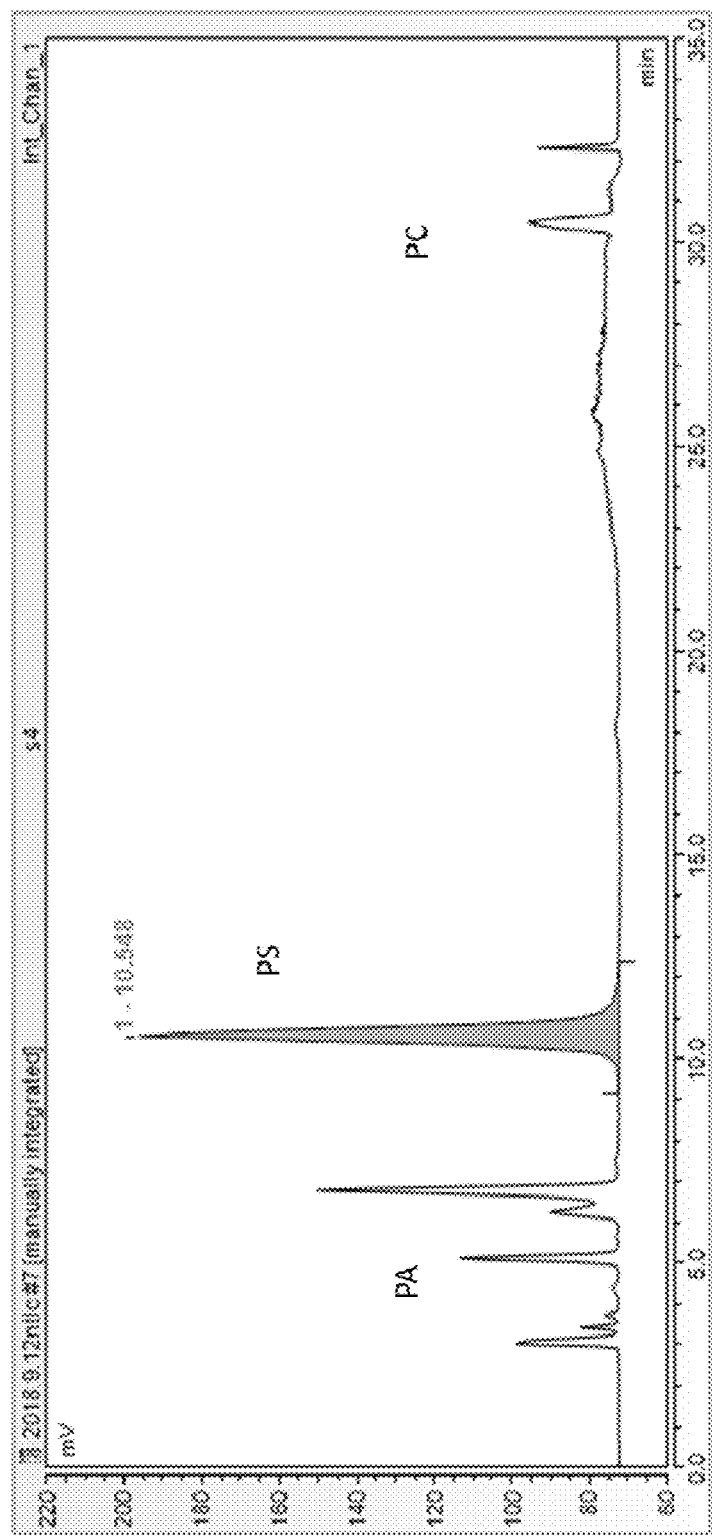
FIG. 2 is a graph showing the results of the reaction of example 2.

Adding the following substances by weight to a container: 200 g of L-serine, 20 g of anhydrous calcium chloride and 500 ml of pure water at a temperature 45° C.; adding 130 g of phospholipid which is soybean phospholipid in which the phosphatidylcholine content is 54%; performing stirring for 5 minutes; adding 25 ml of phospholipase D with the activity of 60 U/ml; applying ultrasound in an enzymatic hydrolysis process, wherein ultrasonic power is 600 W, ultrasonic intensity is 60 W/cm$^2$, ultrasonic frequency is 20 kHz, ultrasonic treatment time is 30 minutes, and enzymatic hydrolysis time is 4 hours. When enzymatic hydrolysis ends, the conversion rate of phosphatidylcholine is 93%, and reaction results are shown in FIG. 2.

Example 3

Figure 3:
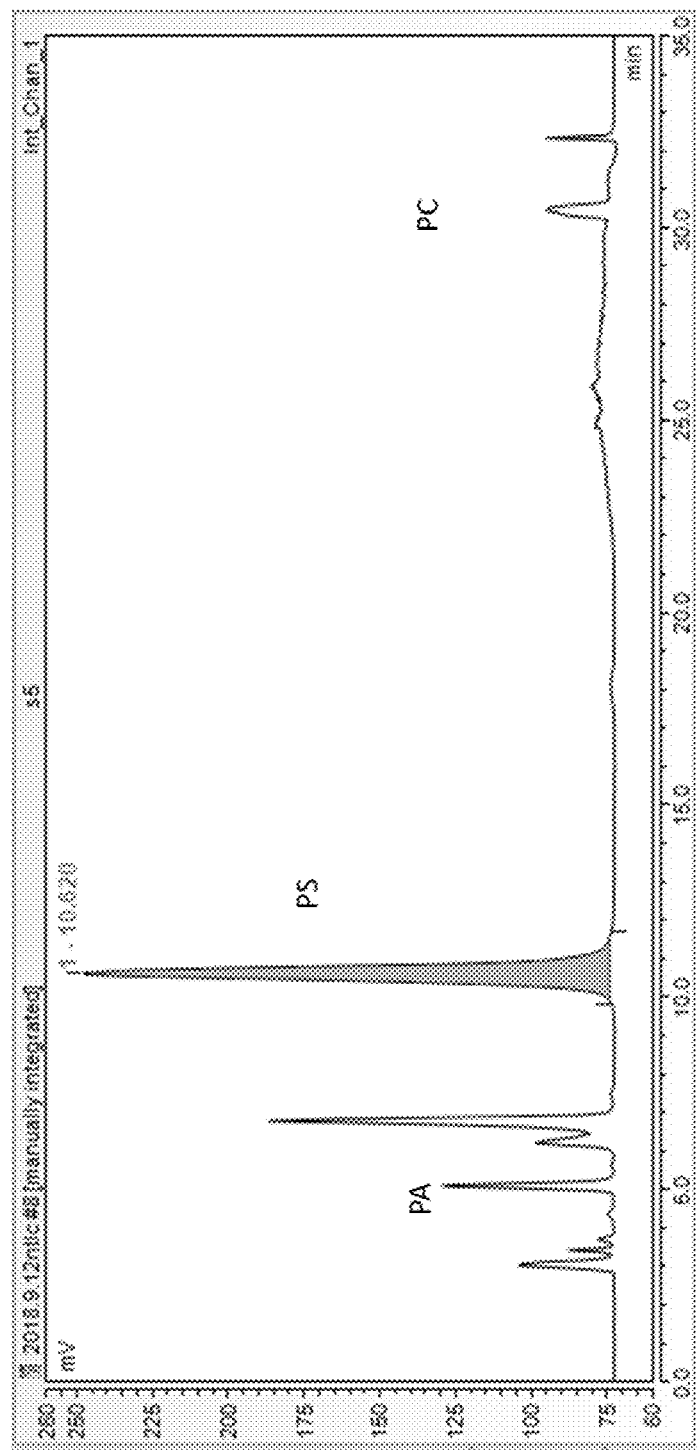
FIG. 3 is a graph showing the results of the reaction of example 3.

Adding the following substances by weight to a container: 180 g of L-serine, 15 g of anhydrous calcium chloride and 450 ml of pure water; performing stirring for 8 minutes at a temperature 40° C.; adding 120 g of phospholipid which is soybean phospholipid in which the phosphatidylcholine content is 54.23%; performing stirring for 5 minutes; adding 25 ml of phospholipase D with the activity of 50 U/ml; applying ultrasound in an enzymatic hydrolysis process, wherein ultrasonic power is 500 W, ultrasonic intensity is 50 W/cm$^2$, ultrasonic frequency is 30 kHz, ultrasonic treatment time is 15 minutes, and enzymatic hydrolysis time is 3 hours. When enzymatic hydrolysis ends, the conversion rate of phosphatidylcholine is 98%, and reaction results are shown in FIG. 3.

Comparative Example 1

Five groups of parallel experiments are designed. The intervention time for applying ultrasound is designed respectively as 0, 0.5, 1, 1.5 and 2 hours at the beginning of an enzymatic hydrolysis reaction, other raw materials and preparation steps are the same as those in example 3, and the conversion rate of phosphatidylcholine when enzymatic hydrolysis ends is shown in table 3:

TABLE 1

Effect of ultrasonic intervention time on conversion rate of phosphatidylcholine

| number | Group | | | |
|---|---|---|---|---|
| Intervention time/h | 1 | 2 | 3 | 4 |
| Intervention time/h | 0 | 0.5 | 1 | 1.5 |
| Conversion rate/% | 98.2 | 95.1 | 90.4 | 80.2 |

It can be seen from the above table that in the phosphatidylcholine enzymatic hydrolysis reaction, when the intervention time for applying ultrasound is 0-0.5 hour at the beginning of the enzymatic hydrolysis reaction, the conversion rate is 95% or higher. When the ultrasound is intervened later than 0.5 hour, the conversion rate drops to 90% or less.

Comparative Example 2

Seven groups of parallel experiments are designed. The enzymatic hydrolysis reaction time is designed respectively as 1.5, 2, 2.5, 3, 3.5, 4 and 4.5 hours, other raw materials and preparation steps are the same as those in example 3, and the conversion rate of phosphatidylcholine when enzymatic hydrolysis ends is shown in table 3:

TABLE 2

Effect of enzymatic hydrolysis time on conversion rate of phosphatidylcholine

| number Enzymatic hydrolysis time/h | Group | | | | | | |
|---|---|---|---|---|---|---|---|
| | 1 | 2 | 3 | 4 | 5 | 6 | 7 |
| Enzymatic hydrolysis time/h | 1.5 | 2 | 2.5 | 3 | 3.5 | 4 | 4.5 |
| Conversion rate/% | 89.3 | 95.2 | 96.6 | 98.5 | 93.4 | 92.7 | 90.8 |

It can be seen from the above table that in the phosphatidylcholine enzymatic hydrolysis reaction, the conversion rate is 92% or higher when ultrasonic treatment time is 2-4 hours, and the conversion rate is 95% or higher when the ultrasonic treatment time is 2-3 hours. When the enzymatic hydrolysis time is less than 2 hours and greater than 4 hours, the conversion rate is greatly reduced.

Comparative Example 3

The experiment uses an $L_{25}$ ($5^6$) orthogonal table, and with ultrasonic frequency (A), ultrasonic intensity (B), ultrasonic power (C), ultrasonic time (D), enzymatic hydrolysis temperature (E) and enzyme activity (F) as six investigation factors, five levels are respectively selected for the experiment. By calculating the average of the experimental data of the 6 factors and 5 levels, range analysis of the results is carried out, the optimal level is selected, the optimal experimental range is compared, and the phosphatidylcholine conversion rate is used as an evaluation index to evaluate the orthogonal experiment. The results are shown in Table 3.

TABLE 3

Orthogonal $L_{25}$ ($5^6$) experimental results and range analysis

| Serial number | Factors | | | | | | Results Conversion rate (%) |
|---|---|---|---|---|---|---|---|
| | A Ultrasonic frequency (kHz) | B Ultrasonic intensity (W/m$^2$) | C Ultrasonic power (W) | D Ultrasonic time (min) | E Temperature (° C.) | F Enzyme activity (U/ml) | |
| 1 | 20 | 30 | 300 | 5 | 25 | 20 | 70.2 |
| 2 | 20 | 40 | 400 | 10 | 35 | 30 | 99.8 |
| 3 | 20 | 50 | 500 | 15 | 45 | 40 | 98.1 |
| 4 | 20 | 60 | 600 | 20 | 55 | 50 | 99.1 |
| 5 | 20 | 70 | 700 | 30 | 65 | 60 | 88.7 |
| 6 | 30 | 30 | 400 | 15 | 55 | 60 | 96.5 |
| 7 | 30 | 40 | 500 | 20 | 65 | 20 | 77.5 |
| 8 | 30 | 50 | 600 | 30 | 25 | 30 | 94.3 |
| 9 | 30 | 60 | 700 | 5 | 35 | 40 | 94.8 |
| 10 | 30 | 70 | 300 | 10 | 45 | 50 | 92.5 |
| 11 | 40 | 30 | 500 | 30 | 35 | 50 | 95.5 |
| 12 | 40 | 40 | 600 | 5 | 45 | 60 | 96.8 |
| 13 | 40 | 50 | 700 | 10 | 55 | 20 | 72.3 |
| 14 | 40 | 60 | 300 | 15 | 65 | 30 | 94.5 |
| 15 | 40 | 70 | 400 | 20 | 25 | 40 | 95.4 |
| 16 | 50 | 30 | 600 | 10 | 65 | 40 | 87.7 |
| 17 | 50 | 40 | 700 | 15 | 25 | 50 | 90.4 |
| 18 | 50 | 50 | 300 | 20 | 35 | 60 | 92.1 |
| 19 | 50 | 60 | 400 | 30 | 45 | 20 | 67.2 |
| 20 | 50 | 70 | 500 | 5 | 55 | 30 | 85.3 |
| 21 | 60 | 30 | 700 | 20 | 45 | 30 | 90.5 |
| 22 | 60 | 40 | 300 | 30 | 55 | 40 | 89.3 |
| 23 | 60 | 50 | 400 | 5 | 65 | 50 | 90.2 |
| 24 | 60 | 60 | 500 | 10 | 25 | 60 | 88.7 |
| 25 | 60 | 70 | 600 | 15 | 35 | 20 | 65.7 |
| $K_1$ | 455.9 | 440.4 | 438.6 | 437.3 | 439.0 | 352.9 | |
| $K_2$ | 455.6 | 453.8 | 449.1 | 441.0 | 447.9 | 464.4 | |
| $K_3$ | 454.5 | 447.0 | 445.1 | 445.2 | 445.1 | 465.3 | |
| $K_4$ | 422.7 | 444.3 | 443.6 | 454.6 | 442.5 | 467.7 | |
| $K_5$ | 424.4 | 427.6 | 436.7 | 435.0 | 438.6 | 462.8 | |
| $\overline{K_1}$ | 91.18 | 88.08 | 87.72 | 87.46 | 87.80 | 70.58 | |
| $\overline{K_2}$ | 91.12 | 90.76 | 89.82 | 88.20 | 89.58 | 92.88 | |
| $\overline{K_3}$ | 90.90 | 89.40 | 89.02 | 89.04 | 89.02 | 93.06 | |
| $\overline{K_4}$ | 84.54 | 88.86 | 88.72 | 90.92 | 88.50 | 93.54 | |
| $\overline{K_5}$ | 84.88 | 85.52 | 87.34 | 87.00 | 87.72 | 92.56 | |
| Optimal level | $A_1$ | $B_2$ | $C_2$ | $D_4$ | $E_2$ | $F_5$ | |
| $R_j$ | 91.18 | 90.76 | 89.82 | 90.92 | 89.58 | 93.54 | |
| Primary and secondary order | | | | FADBCE | | | |

From the range analysis of the orthogonal experiment, the primary and secondary order of the influences of the six factors on the conversion rate is F>A>D>B>C>E, and based on variance analysis, the optimal experimental conditions are: $A_1B_2C_2D_4E_2F_5$, that is, the ultrasonic frequency is 20 kHz, the ultrasonic intensity is 40 W/m$^2$, the ultrasonic power is 400 W, the ultrasonic time is 20 min, the enzymatic hydrolysis temperature is 35° C., and the enzyme activity is 50 U/ml. According to the sum of the same level of experiments of factor A (ultrasonic frequency), it can be seen that $K_1>K_2>K_3>K_5>K_4$, the preferred ultrasonic frequency range is 20-40 kHz, and the more preferred the ultrasonic frequency range is 20-30 kHz; according to the sum of the same level of experiments of factor B (ultrasonic intensity), it can be seen that $K_2>K_3>K_4>K_1>K_5$, the preferred ultrasonic intensity range is 40-60 W/m$^2$, and more preferably the ultrasonic intensity range is 40-50 W/m$^2$; according to the sum of the same level of experiments of factor C (ultrasonic power), it can be seen that $K_2>K_3>K_4>K_1>K_5$, the preferred ultrasonic power range is 400-600 W, and the more preferred ultrasonic power range is 400-500 W; according to the sum of the same level of experiments of factor D (ultrasonic time), it can be seen that $K_4>K_3>K_2>K_1>K_5$, the preferred ultrasonic time range is 10-20 min, and the more preferred ultrasonic time range is 15-20 min; according to the sum of the same level of experiments of factor E (temperature), it can be seen that $K_2>K_3>K_4>K_1>K_5$, the preferred ultrasonic temperature range is 35-55° C., and the more preferable ultrasonic temperature range is 35-45° C.; and according to the sum of the same level of experiments of factor F (enzyme activity), it can be seen that $K_4>K_3>K_2>K_5>K_1$, the preferred enzyme activity range is 30-60 U/ml, and the more preferred enzyme activity range is 30-50 U/ml.

What is claimed is:

1. An ultrasound-assisted method for preparing phosphatidylserine characterized by comprising the following steps: (i) adding a phospholipid into a mixture that comprises L-serine, anhydrous calcium chloride and water, and (ii) adding phospholipase D to the mixture to start an enzymatic hydrolysis reaction that would yield the phosphatidylserine, wherein said method requires applying ultrasound waves 30 minutes after starting the enzymatic hydrolysis reaction, wherein the ultrasound waves are applied for 15-20 minutes.

2. The ultrasonic-assisted method for preparing phosphatidylserine of claim 1, wherein the ultrasonic frequency is 20-40 kHz; the ultrasonic intensity is 40-60 $W/m^2$; and the ultrasonic power is 400-600 W.

3. The ultrasonic-assisted method for preparing phosphatidylserine of claim 2, wherein the ultrasonic frequency is 20-30 kHz; the ultrasonic intensity is 40-50 $W/m^2$; and the ultrasonic power is 400-500 W.

4. The ultrasonic-assisted method for preparing phosphatidylserine of claim 1, wherein the time of the enzymatic hydrolysis reaction is 2-4 hours.

5. The ultrasonic-assisted method for preparing phosphatidylserine of claim 4, wherein the time of the enzymatic hydrolysis reaction is 2-3 hours.

6. The ultrasonic-assisted method for preparing phosphatidylserine of claim 1, wherein the temperature at the start of enzymatic hydrolysis is 35-45° C.

7. The ultrasonic-assisted method for preparing phosphatidylserine of claim 1, wherein the phospholipid is soybean phospholipid in which the phosphatidylcholine content is 54-55%.

\* \* \* \* \*